(12) United States Patent
Yong et al.

(10) Patent No.: US 12,161,773 B2
(45) Date of Patent: Dec. 10, 2024

(54) PUFF STERILIZATION PATCH

(71) Applicant: Won Ju Yong, Paju-si (KR)

(72) Inventors: Won Ju Yong, Paju-si (KR); Gyeong Jung Yun, Paju-si (KR)

( * ) Notice: Subject to any disclaimer, the term of this patent is extended or adjusted under 35 U.S.C. 154(b) by 697 days.

(21) Appl. No.: 17/433,940

(22) PCT Filed: Feb. 21, 2020

(86) PCT No.: PCT/KR2020/002525
§ 371 (c)(1),
(2) Date: Aug. 25, 2021

(87) PCT Pub. No.: WO2020/175858
PCT Pub. Date: Sep. 3, 2020

(65) Prior Publication Data
US 2022/0143248 A1    May 12, 2022

(30) Foreign Application Priority Data
Feb. 25, 2019    (KR) ........................ 10-2019-0021853

(51) Int. Cl.
| | | |
|---|---|---|
| D03D 15/283 | (2021.01) | |
| A45D 33/00 | (2006.01) | |
| A61L 2/232 | (2006.01) | |
| A61L 2/238 | (2006.01) | |
| D03D 9/00 | (2006.01) | |

(Continued)

(52) U.S. Cl.
CPC ............ *A61L 2/238* (2013.01); *A45D 33/006* (2013.01); *A61L 2/232* (2013.01); *D03D 9/00* (2013.01); *D03D 15/25* (2021.01); *D03D 15/283* (2021.01); *D04B 1/16* (2013.01); *A45D 2033/001* (2013.01); *A61L 2101/26* (2020.08); *A61L 2202/16* (2013.01)

(58) Field of Classification Search
None
See application file for complete search history.

(56) References Cited

U.S. PATENT DOCUMENTS

| 5,595,750 A | 1/1997 | Jacobson et al. |
| 6,124,221 A * | 9/2000 | Gabbay ................. F41H 5/0471 |
| | | 442/379 |
| 6,274,519 B1 * | 8/2001 | Omori .................... B65D 81/24 |
| | | 442/212 |

FOREIGN PATENT DOCUMENTS

| JP | S58190915 U | 12/1983 |
| JP | H08505858 A | 6/1996 |

(Continued)

OTHER PUBLICATIONS

WO 2019039823-A1 English Machine Translation. (Year: 2019).*

*Primary Examiner* — Jenna L Johnson
(74) *Attorney, Agent, or Firm* — Rabin & Berdo, P.C.

(57) ABSTRACT

The present invention relates to a puff sterilization patch and, particularly, to a puff sterilization patch which is manufactured in the form of a net or fabric by using yarns made of copper having sterilizing power and can be attached to a cosmetic container so as to sterilize a puff. To this end, the present invention comprises: a pad layer formed by weaving wefts and warps into a net, wherein the wefts mainly comprise yarns made of copper and are arranged at regular intervals, and the warps mainly comprise yarns made of a synthetic resin material and are arranged at regular intervals: and an adhesive layer provided on the underside surface of the pad layer.

5 Claims, 4 Drawing Sheets

(51) Int. Cl.
    *D03D 15/25*    (2021.01)
    *D04B 1/16*     (2006.01)
    *A61L 101/26*   (2006.01)

(56)            References Cited

FOREIGN PATENT DOCUMENTS

KR      1020170101827 A      9/2017
KR       101804172 B1       12/2017
KR       101844742 B1        4/2018
KR       101877240 B1        7/2018
KR       102005818 B1        8/2019
WO      WO-2019039823 A1 *   2/2019   ............. A01N 59/20

* cited by examiner

PUFF STERILIZATION PATCH

TECHNICAL FIELD

The present invention relates to a puff sterilization patch, and more particularly, to a puff sterilization patch which is manufactured in the form of a net or fabric by using yarns made of copper having sterilizing power and is thus attachable to a cosmetic container so as to sterilize a puff.

BACKGROUND ART

As disclosed in Korean Patent No. 10-1877240 (entitled "Cosmetic container capable of using puff in clean state"), a cosmetic container is configured to have a puff seating space formed on a container cover for opening and closing top of a container body accommodating foundation to seat a puff thereinto and an antibacterial member located in the puff seating space, so that if the puff is placed on top of the antibacterial member within the puff seating space, it is sterilized and is thus kept clean.

The antibacterial member contains silver nanoparticles to provide sterilizing power, and through the sterilizing power, the puff may be sterilized.

However, since the antibacterial member in the conventional technology contains silver nanoparticles, it may be easily discolored by the contact with air, and further, if the silver nanoparticles separated from the antibacterial member are applied to a user's skin, they permeate into the skin to cause even skin necrosis.

Besides, the antibacterial member containing silver nanoparticles is relatively expensive.

PRIOR ART DOCUMENT

Korean Patent No. 10-1877240

Cosmetic Container Capable of Using Puff in Clean State

DISCLOSURE

Technical Problem

Accordingly, the present invention has been made in view of the above-mentioned problems occurring in the related art, and it is an object of the present invention to provide a puff sterilization patch that can be manufactured in the form of a net or fabric by using yarns made of copper, thereby giving no harm to the human body and providing a low manufacturing cost.

Technical Solution

To accomplish the above-mentioned object, according to one aspect of the present invention, there is provided a puff sterilization patch including: a pad layer formed by weaving wefts and warps into a net, the wefts mainly comprising yarns made of copper in such a manner as to be arranged at regular intervals, and the warps mainly comprising yarns made of a synthetic resin material in such a manner as to be arranged at regular intervals; and an adhesive layer provided on the underside of the pad layer.

To accomplish the above-mentioned object, according to another aspect of the present invention, there is provided a puff sterilization patch including: a pad layer formed by weaving or knitting copper yarns into a net or fabric, the copper yarns being made by coating copper particles on nylon yarns; and an adhesive layer provided on the underside of the pad layer.

Advantageous Effects

According to the present invention, the puff sterilization patch can be manufactured in the form of a net or fabric by using yarns made of copper, thereby giving no harm the human body, while maintaining a sterilization force thereof, and providing a ow manufacturing cost.

EXPLANATIONS OF REFERENCE NUMERALS

Figure 1:
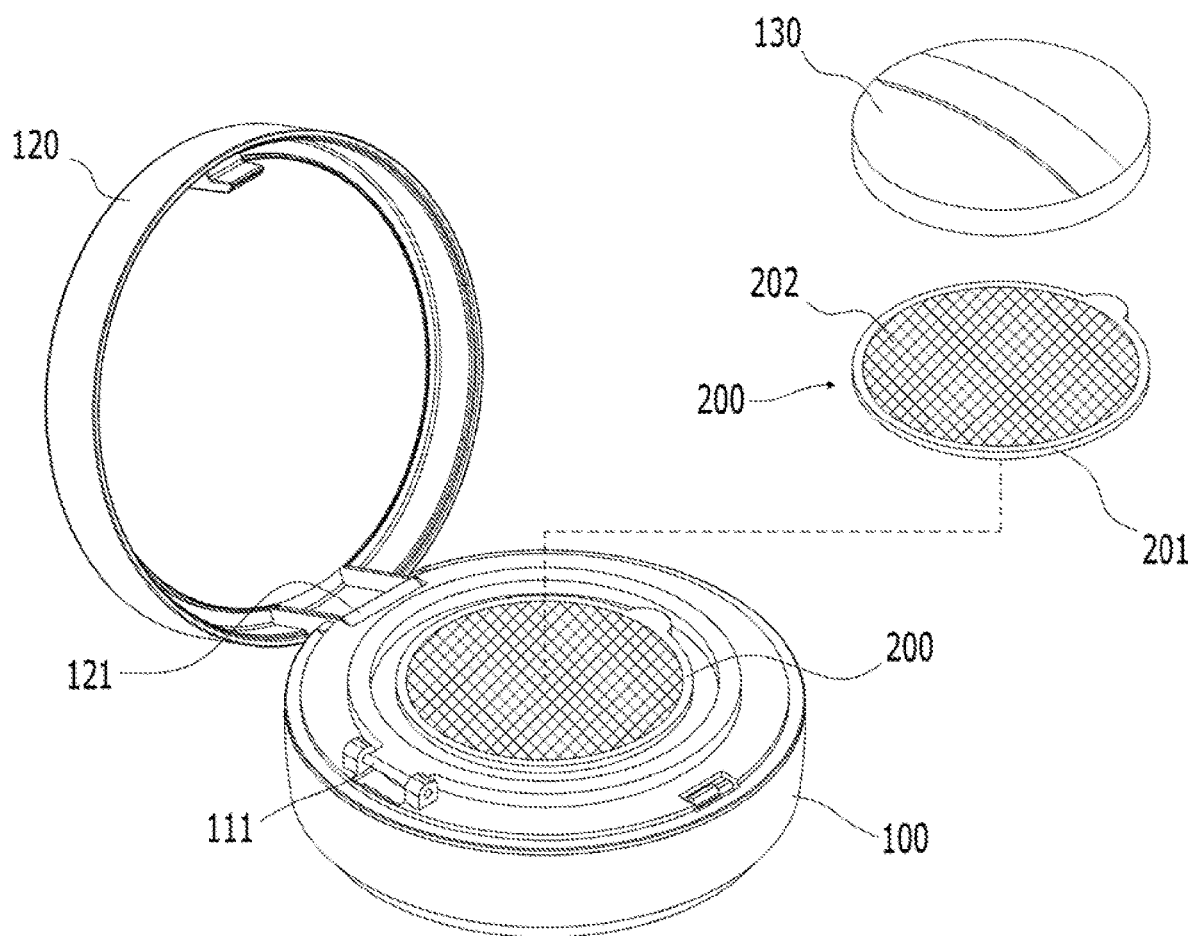
FIG. 1 is a perspective view showing a puff sterilization patch according to the present invention and a cosmetic container with the puff sterilization patch.

100: Body
110: Puff accommodation space
111: Hinge
120: Upper cover
121: Hinge
130: Puff
200: Sterilization patch
201: Adhesive layer
202: Pad layer
210, 230, 250: Adhesive layer
220, 240, 260: Pad layer

BEST MODE FOR INVENTION

A puff sterilization batch according to the present invention includes a pad layer formed by weaving wefts and warps into a net, the wefts mainly comprising yarns made of copper in such a manner as to be arranged at regular intervals, and the warps mainly comprising yarns made of a synthetic resin material in such a manner as to be arranged at regular intervals, and an adhesive layer provided on the underside of the pad layer.

Mode For Invention

Objects, characteristics and advantages of the present invention will be more clearly understood from the detailed description as will be described below and the attached drawings, and those skilled in the art can easily change or modify the embodiments without departing from the scope and spirit of the present invention.

In the description, if it is determined that the detailed explanation on the well known technology related to the present invention makes the scope of the present invention not clear, the explanation will be avoided for the brevity of the description.

Further, the terms used herein are defined as general terms widely used at present in accordance with the functions of the present invention, but may be varied under the intention or regulation of a user or operator.

In specific cases, further, terms may be arbitrarily defined by an applicant, but their meaning will be described in detail in the detailed description of the present invention.

Therefore, the terms used herein should be defined, not as simple names, on the basis of their meaning and the whole scope of the present invention.

Hereinafter, embodiments of the present invention will be explained in detail with reference to the attached drawings.

However, the present invention may be modified in various ways and may have several exemplary embodiments, and the idea and scope of the invention is not limited to the embodiments as will be discussed later.

The embodiments of the present invention are provided to more fully explain the invention to those having ordinary skill in the art.

FIG. 1 is a perspective view showing a puff sterilization patch according to the present invention and a cosmetic container with the puff sterilization patch, and the cosmetic container includes a body 100 adapted to accommodate a cosmetic material like foundation applied with a puff 130 therein and a puff accommodation cover 110 located on top of the body 100 to open and close the interior of the body 100 by means of a hinge 111.

The puff accommodation cover 110 has a puff accommodation space 110 adapted to accommodatedly seat the puff 130 therein, and the body 100 has an upper cover 120 adapted to open and close the puff accommodation space 110 in such a manner as to be rotatable by means of a hinge 121.

A sterilization patch 200 is attached to the bottom of the puff accommodation space 110 and includes a circular pad layer 202 woven or knitted in the form of a net or fabric by using yarns made of copper and yarns made of a synthetic resin material such as PE, PP, PC, and the like and an adhesive layer 201 located on the underside of the pad layer 202 in such a manner as to repeatedly attach and detach the pad layer 202 thereto and therefrom.

The adhesive layer 201 may be an adhesive tape.

Accordingly, the adhesive layer 202 of the sterilization patch 200 is attached to the puff accommodation space 110, and next, if the puff 130 is kept placed on top of the sterilization patch 200, sterilization can be performed by the copper yarns having sterilizing power.

Figure 2:
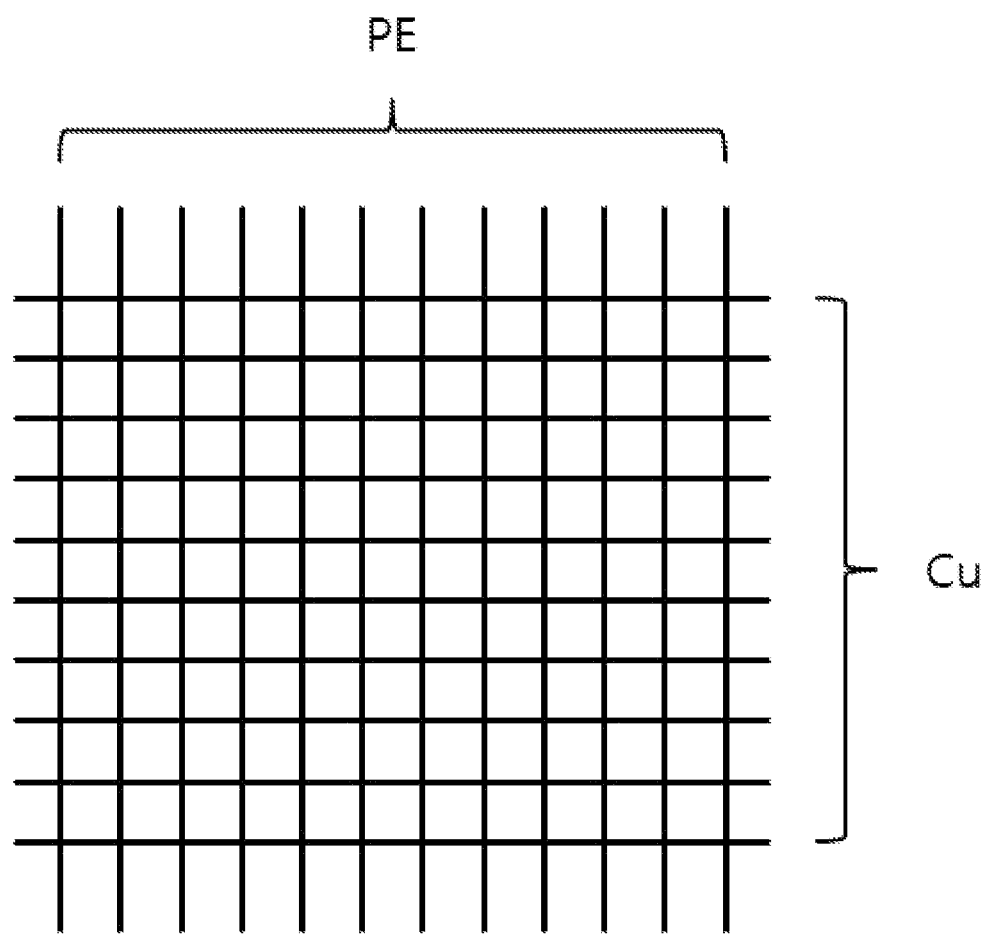
FIG. 2 is a schematic view showing a knitted structure of the puff sterilization patch according to the present invention.

As shown in FIG. 2, the pad layer 202 is formed by arranging wefts transversely at regular intervals and arranging warps longitudinally at regular intervals. The copper yarns are arranged as the wefts, and the yarns made of the synthetic resin material are arranged as the warps.

For example, only the copper yarns are arranged as the wefts, and otherwise, the copper yarns and the yarns made of the synthetic resin material are alternately arranged as the wefts. Further, only the yarns made of the synthetic resin material are arranged as the warps, and otherwise, the yarns made of the synthetic resin material and the copper yarns are alternately arranged as the warps.

This is to easily weave the pad layer 202, while keeping the sterilizing power by means of the components of the copper yarns, and in this case, the copper yarns are made by coating copper particles onto the outer peripheries of nylon yarns by means of thermal compression or spraying. In this case, if only the copper yarns are arranged as the wefts and warps, the copper particles of the copper yarns arranged as the wefts and warps are frictional to one another, while being woven, so that they may fall out thereby lowering the sterilizing power, and further, the manufacturing cost may be raised.

However, the pad layer 202 is woven in the form of a net by using the copper yarns arranged as the wefts and the yarns made of the synthetic resin material arranged as the warps, thereby avoiding the friction among the copper yarns and preventing the copper particles from falling out from the copper yarns.

Of course, only the copper yarns can be arranged as both of the wefts and the warps, and in this case, the pad layer 202 is knitted to the form of a fabric, not to the form of a net.

The copper yarns desirably are 70 denier yarns, and the yarns made of the synthetic resin PE desirably are 100 denier yarns.

In this case, a denier is a unit of measurement that expresses yarn thickness, and when the yarn length is 450 m and its weight is 0.05 g, it is 1 denier.

Accordingly, the pad layer 202 is formed by using the copper yarns and the yarns made of the synthetic resin material, so that the sterilization patch 200 gives no harm to the human body and has a low manufacturing cost.

A release paper is attached to the underside of the adhesive layer 201 and is thus removed from the adhesive layer 201 when the sterilization patch 200 is attached to the puff accommodation space 110.

Before the adhesive layer 201 is located on the underside of the pad layer 202 after the pad layer 202 has been manufactured, further, a synthetic resin film like a PET film or a plate-shaped silicone may be first attached to the underside of the pad layer 202 to allow the pad layer 202 to be kept uniformly stretched. Next, the adhesive layer 201, that is, the adhesive tape is attached to the film or silicone.

Figure 5:
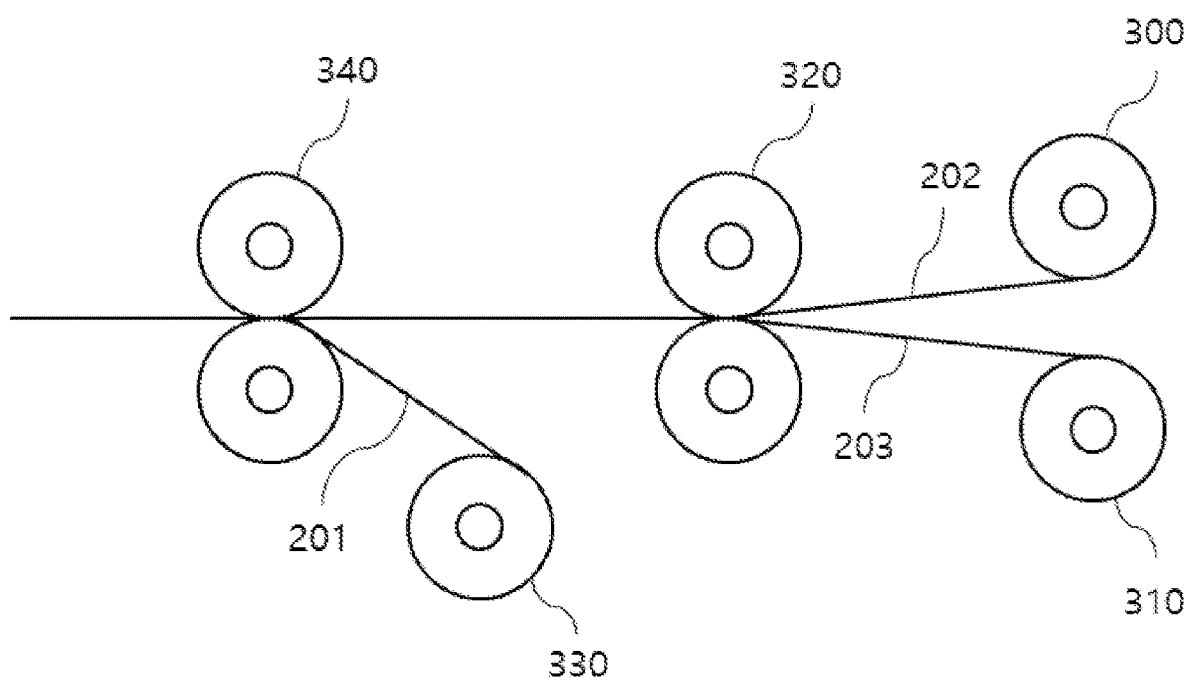
FIG. 5 is a schematic view showing a process of manufacturing the puff sterilization patch according to the present invention.

To allow the PET film to be attached to the underside of the pad layer 202, as shown in FIG. 5, the fabric-shaped pad layer 202 is wound on a first roll 300, and a PET film 203 is wound on a second roll 310. In this state, the PET film 203 is laid on the underside of the pad layer 202 and is then transferred to a press 320 having two compression rolls, so that it becomes compressed.

In the state where the Phi film 203 and the pad layer 202 are compressed against each other, after that, the adhesive layer 201 wound on a third roll 330 is attached to the underside of the PET film 203 by means of compression rolls 340.

In this case, the release paper is attached to the underside of the adhesive layer 201, and after the release paper is removed from the adhesive layer 201, accordingly, the adhesive layer 201 is attached to the puff accommodation space 110.

Accordingly, the fabric made by laminating the pad layer 202, the PET film 203, and the adhesive layer 201 is cut off by a press to have a circular shape, thereby manufacturing one sterilization patch 200.

If the silicone is attached, instead of the PET film 203, the pad layer 202 is attached to a circular silicone plate and is then compressed through a thermal compressor having a temperature of 300 to 340° C.

Figure 3:
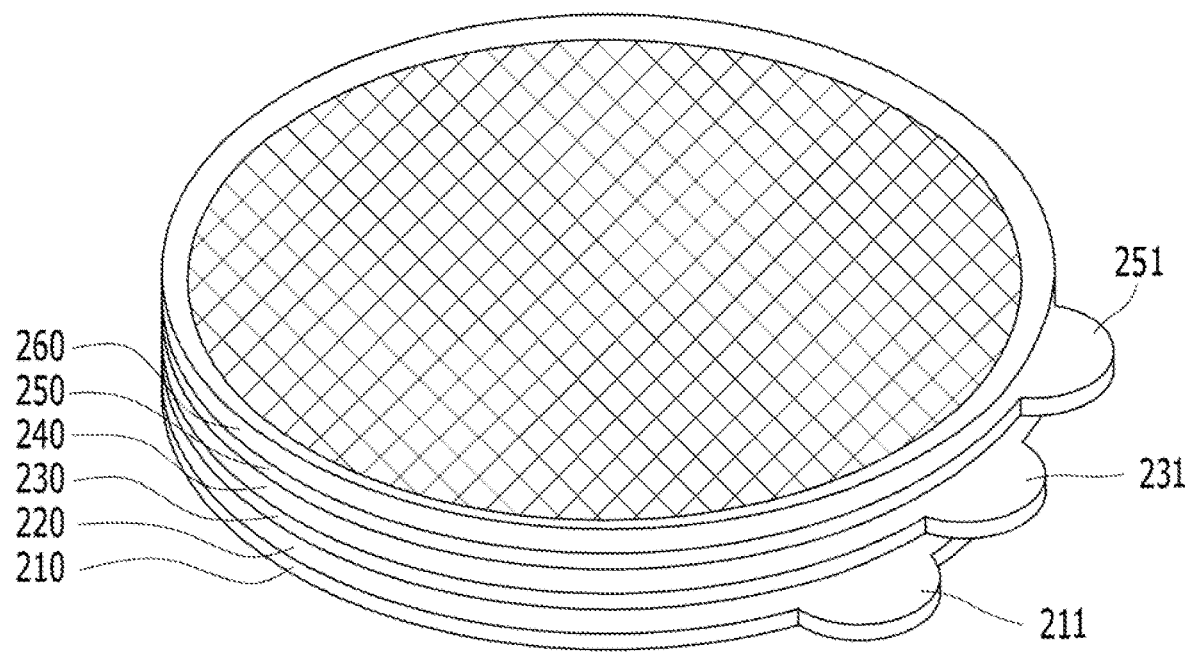
FIG. 3 is a perspective view showing a plurality of puff sterilization patches laminated on top of each other.

FIG. 3 is a perspective view showing a multi-layered sterilization patch 200 according to the present invention. Generally, the single sterilization patch 200 having the net-shaped pad layer 202 is attached to the puff accommodation space 110, and next, the puff 130 is placed on the top of the pad layer 202. In this case, a cosmetic material such as solid, liquid, or gel type foundation may be applied to the puff 130 used, and through the use of the puff 130, the cosmetic material may be applied or caught to the net-shaped pad layer 202, thereby undesirably causing the copper yarns to be buried into the cosmetic material.

As a result, the sterilizing power of the copper yarns becomes deteriorated, which makes the normal function of the sterilization patch lost.

Accordingly, the pad layer located at the topmost position of a plurality of pad layers stacked is first removed from the plurality of pad layers stacked, and next, the plurality of pad layers stacked are removed one by one, without the inconvenient exchange of the sterilization patch 200 whose sterilizing power becomes bad into new one, so that the pad layers can be used for a long period of time in a clean state.

To provide the multi-layered sterilization patch 200 according to the present invention, accordingly, a first adhesive layer 210, a first pad layer 220, a second adhesive layer 230, a second pad layer 240, a third adhesive layer 250, and a third pad layer 260 are laminated sequentially on each other in the order mentioned in an up direction thereof.

Further, the respective adhesive layers 210, 230, and 250 have tags 211, 231, and 251 protruding laterally therefrom in such a manner as to be not laid on top of each other.

Figure 4:
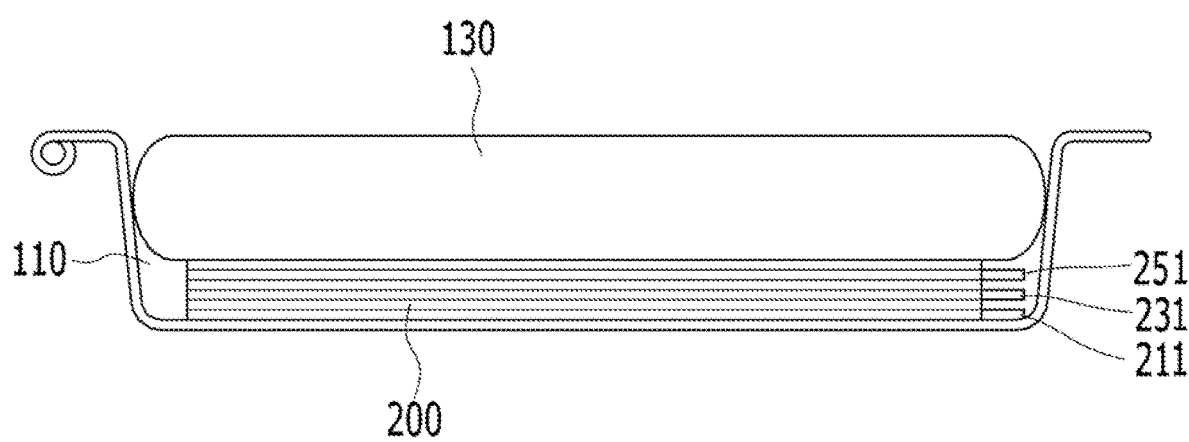
FIG. 4 is a sectional view showing a state where the laminated puff sterilization patches are attached to a puff accommodation space.

Accordingly, as shown in FIG. 4, the multi-layered sterilization patch 200 is attached to the puff accommodation space 110, and next, the puff 130 is placed on the top of the multi-layered sterilization patch 200. In this case, if the third pad layer 260 placed on top of the multi-layered sterilization patch 200 becomes contaminated, it is torn off by pulling the tag 251 so that the third adhesive layer 250 is separated and removed from the second pad layer 240.

As a result, the second pad layer 240 not contaminated is exposed to the outside and thus serves to sterilize the puff 130.

In the same manner as above, if the second pad layer 240 becomes contaminated, it is removed by the above-mentioned process, so that the first pad layer 220 not contaminated is exposed to the outside.

Although specific embodiments have been illustrated and described herein, it will be appreciated by those of ordinary skill in the art that any arrangement, which is calculated to achieve the same purpose, may be substituted for the specific embodiments shown. This application is intended to cover any adaptations or variations of the present invention.

Therefore, it is manifestly intended that his invention be limited only by the claims and the equivalents thereof.

The invention claimed is:

1. A puff sterilization patch comprising:
   a pad layer formed by weaving wefts and warps into a net, the wefts comprising yarns made of copper in such a manner as to be arranged at regular intervals, and the warps comprising yarns made of a synthetic resin material in such a manner as to be arranged at regular intervals; and
   an adhesive layer provided on the underside of the pad layer,
   wherein the pad layer has a synthetic resin film or silicone attached to the underside thereof so that the adhesive layer is attached to the underside of the film or silicone.

2. A puff sterilization patch comprising: a pad layer formed by weaving or knitting copper yarns into a net or fabric, the copper yarns being made by coating copper particles on nylon yarns; and an adhesive layer provided on the underside of the pad layer, wherein the pad layer has a synthetic resin film or silicone attached to the underside thereof so that the adhesive layer is attached to the underside of the film or silicone.

3. The puff sterilization patch according to claim 1, wherein a plurality of pad layers and a plurality of adhesive layers are laminated to form multiple layers.

4. The puff sterilization patch according to claim 1, wherein the wefts or warps are woven by alternating the yarns made of copper and the yarns made of the synthetic resin material with each other.

5. The puff sterilization patch according to claim 2, wherein a plurality of pad layers and a plurality of adhesive layers are laminated to form multiple layers.

* * * * *